United States Patent [19]

Czernecki et al.

[11] Patent Number: 5,101,023

[45] Date of Patent: Mar. 31, 1992

[54] PROCESS FOR SYNTHESISING AZIDO-3'-DEOXYTHYMIDINE AND ANALOGS

[75] Inventors: Stanislas Czernecki, Maincy; Jean-Marc Valery, Nandy; Guy Ville, Paris, all of France

[73] Assignee: Universite Pierre et Marie Curie (Paris VI), Paris, France

[21] Appl. No.: 415,241

[22] PCT Filed: Jan. 19, 1989

[86] PCT No.: PCTFR89/00018

§ 371 Date: May 4, 1990

§ 102(e) Date: May 4, 1990

[30] Foreign Application Priority Data

Jan. 19, 1988 [FR] France .................... 88 00553
Dec. 9, 1988 [FR] France .................... 88 16248

[51] Int. Cl.$^5$ ............................. C07H 19/073
[52] U.S. Cl. ................................... 536/23
[58] Field of Search ........................ 536/23

[56] References Cited

U.S. PATENT DOCUMENTS 4,681,933 7/1987 Chu ........................... 536/23

FOREIGN PATENT DOCUMENTS 0199451 10/1986 European Pat. Off. .

OTHER PUBLICATIONS

Chemical Abstracts, vol. 92, 1980, p. 716, resume No. 198690r, Columbus, Ohio, U.S.
K. A. Watanabe et al.: "2,5'-Anhydrouridine and 2,5'-Anhydro-5-Fluorouridine, One-Step Conversion of Uridine and 5-Fluorouridine into their Corresponding 2,5'-Anhyronucleosides", & Nucl. Acid. Chem. 1978, 1, 343–346.
Journal of Organic Chemistry, vol. 35, No. 9, 1970, pp. 2868–2877; J. P. F. Verheyden et al.: "Halo Sugar Nucleosides. II, Iodination of Secondary Hydroxyl Groups of Nucleosides with Methyltriphenoxyphosphonium Iodide", p. 2869.
Chemical Abstracts, vol. 91, 1979, p. 623, resume No. 74826z, Columbus, Ohio, U.S.; J. Kimura et al.: "Studies on Nucleosides and Nucleotides. VII".
"Prepration of Pyrimidine Nucleoside 5'-Phosphates and N3,5'-Purine Cyclonucleosides by Selective Activation of the 5' Hydroxyl Group", and Bull, Chem. Soc. JPN. 1979, 52(4), 1191–1196.
Chemical Abstracts, vol. 101, No. 21, Nov. 1984, p. 813, resume No. 192378c, Columbus, Ohio, U.S..
V. F. Zaitseva et al.: "Aminonucleosides and their Derivatives, XI, Synthesis of 3'-Amino-2',3'-Dideoxynucleoside 5'-Triphosphates", Bioorg. Khim 1984, 10(5), 670–680.
Journal of the Chemical society, Perkin Transactions I, pp. 306–310, London, GB.
I. Yamamoto et al.: "One-Step Synthesis of 5'-Azido–Nucleosides", p. 306.
(List continued on next page.)

Primary Examiner—Cecilia Shen
Attorney, Agent, or Firm—Cushman, Darby & Cushman

[57] ABSTRACT

The invention relates to a process for preparing a compound of formula (I)

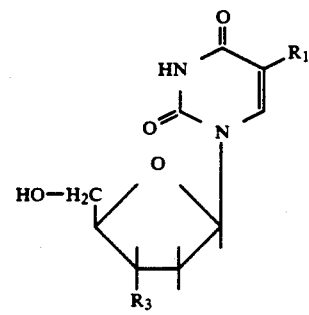

in which $R_1$ is H, an alkyl radical or an alkoxy, hydroxyalkyl or halogen radical, and $R_3$ is $N_3$ or a CN radical, characterized in that a compound of formula (II):

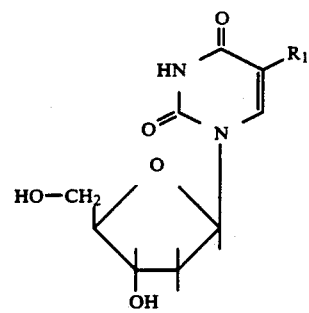

is reacted with a phosphine derivative and an azodicarboxylic acid diester and a carboxylic acid $R_2$—COOH in a solvent compatible with the reaction conditions, to form the compound of formula (III):

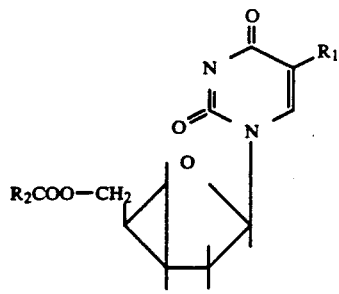

which, after separation if required, is opened in the presence of an azide or a cyanide in a solvent compatible with the reaction conditions, and the compound of formula (I) is then isolated from the reaction medium after deprotection of the 5'-position.

15 Claims, No Drawings

OTHER PUBLICATIONS

Chemical Abstract No. 198690r, vol. 92, "2,5'-Anhydrouridine and 2,5'-Anhydro-5-Fluorouridine, One-Step Conversion of Uridine and 5-Fluorouridine into their Corresponding 2,5'-Anhydronucleosides" (1980), p. 716.

Chemical Abstract, Watanabe et al., "2,5'-Anhydrouridine and 2,5'-Anhydro-5-Fluorouridine, One-Step Conversion of Uridine and 5-Fluorouridine into their Corresponding 2,5'-Anhydronucleosides", *Nucl. Acid Chem.*, vol. 1, (1978), pp. 343-346.

Verheyden et al., "Halo Sugar Necleosides, II, Iodination of Secondary Hydroxyl Groups of Nucleosides with Methyltriphenoxy-Phosphonium Iodine", Journal of Organic Chemistry, vol. 35, Nr. 9, (1970), pp. 2868-2877.

Chemical Abstract No. 74826z, vol. 91, "Studies on Nucleosides and Nucleotides, VII, Prepartion or Pyrimidine Nucleoside 5'-Phosphates and N3,5'-Purine Cyclonucleosides by Selective Activation of the 5'-Hydroxyl Group", (1979), p. 623.

Chemical Abstract, Kimura et al., "Studies on Nucelosides and Nucleotides, VII, Cyclonucleosides by Selective Activation of the 5'-Hydroxyl Group", *Chem. Soc. Jpn.*, vol. 52, 4, (1979), pp. 1191-1196.

Chemical Abstract No. 192378c, vol. 101, Nr 21, "Amino-Nucleosides and their Derivatives, XI, Snythesis of 3'-Amino-2',3'-Dideoxynucleoside 5'-Triphosphates", (1984), p. 813.

Chemical Abstract, Zaitseva et al., "Amino-Nucleosides and their Derivatives, XI, Synthesis of 3'-Amino-2',3'-Dideoxynucleoside 5'-Triphosphates", *Bioorg. Khim*, vol. 10, 5, (1984), pp. 670-680.

Yamamoto et al. "One-Step Synthesis of 5'-Azido-Nucleosides", *Journal of Chemical Society*, Perkin Transactions I, (London, GB), (1980), pp. 306-310.

Ajmera et al., CA100-19719w (1984).
Joecks et al., CA100-21031p (1984).3
Pankiewicz et al., CA109-55145a (1988).
Matthes et al., CA109-55173h (1988).
Czernecki et al., CA112-56586u (1990).
Gaertner et al., CA112-56594v (1990).

PROCESS FOR SYNTHESISING AZIDO-3'-DEOXYTHYMIDINE AND ANALOGS

The present invention relates to a process for the synthesis of 3'-azido-3'-deoxythymidine (azidothymidine, AZT, zidovudine) and of related compounds used in combating AIDS.

A marketing authorization has recently been granted to the Wellcome Firm for the marketing of a product based on azidothymidine. The therapeutic application of this product is described in Patent DE-3,608,606.

Different syntheses of AZT have been described to date; they have the common feature of starting from thymidine and of comprising a rather large number of stages, between five and seven, except for one synthesis which requires the use of an expensive base.

These syntheses are summarized, for example, in the paper in Drugs of the Future, vol. 11, No. 12 (1986); the conversion yields are very low in all cases.

A paper published in 1984 (V. E. Zaitseva et al., Bioorg. Khim., 10, 670 (1984)) described a synthesis of AZT employing three stages; it appears, nevertheless, that this process has not been developed.

In effect, the second stage of the process requires the preparation of lithium p-methylbenzoate, and the isolation of the AZT obtained in the final stage is carried out by column chromatography.

The subject of the present invention is a process for preparing AZT and related compounds which employs only two stages and which, in addition, has the enormous advantage of being able to be performed in a single reaction vessel, if necessary.

More especially, the subject of the invention is a process for preparing a compound of formula (I):

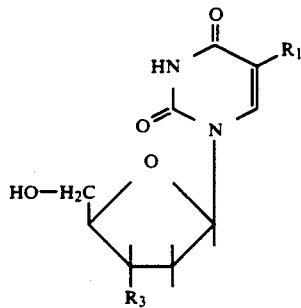

in which $R_1$ is H, an alkyl radical or an alkoxy, hydroxyalkyl or halogen radical, and $R_3$ is $N_3$ or a CN radical, characterized in that a compound of formula (II):

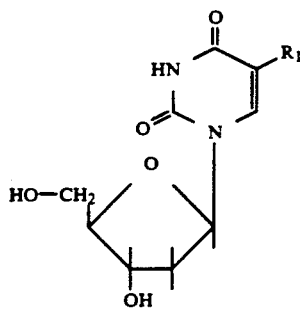

is reacted with a phosphine or phosphite derivative and an azodicarboxylic acid diester and a carboxylic acid $R_2$—COOH in a solvent compatible with the reaction conditions, to form the compound of formula (III):

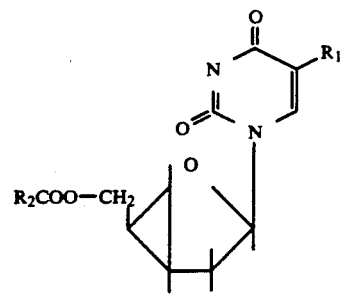

which, after separation if required, is opened in the presence of an azide or a cyanide in a solvent compatible with the reaction conditions, and the compound of formula (I) is then isolated from the reaction medium after deprotection of the 5'-position.

The preparation of a compound of formula III with $R_1$ denoting a methyl group and $R_2$ a phenyl group has been mentioned in the literature (Kimura et al., Bull. of the Chem. Soc. of Japan Vol. 52 (4), 1979, p. 1191), but the process in question is not satisfactory since it requires two stages and leads to a low yield, of the order of 35%.

Naturally, among the compounds of formula (I), AZT, that is to say the compound in which $R_1$ is equal to $CH_3$ and $R_3$ is equal to $N_3$, must be mentioned more especially, nevertheless, at the present time, other AZT derivatives are being developed, these comprising, in particular, derivatives in which R is equal to a lower alkyl radical or a lower alkoxy or lower hydroxyalkyl radical, containing from 1 to 5 carbon atoms, for example methyl or ethyl radicals.

In the process according to the present invention, the starting material, in particular for preparing AZT, is thymidine, a compound which is industrially available and which must preferably, for the requirements of the process, be in general dehydrated since the presence of water considerably impairs the yield of the process.

Among the other reactants used for the preparation of a compound of formula III, although it is possible to use different types of phosphine or phosphite, the preferred phosphine is triphenylphosphine since it is a product which is readily available at the industrial level. Similarly, the azodicarboxylic acid diesters can be alkyl or aryl esters, especially lower alkyl esters such as diethyl azodicarboxylate (DEAD) or preferably diisopropyl azodicarboxylate (DIAD). This compound DIAD is, in effect, a compound which is inexpensive and which enables yields to be obtained which are equal or sometimes even greater than those obtained with other diesters.

Finally, in the choice of carboxylic acid, $R_2$—COOH, $R_2$ denotes an aliphatic radical and its derivatives or preferably an aromatic radical and its derivatives. Aromatic radical is understood to mean radicals such as phenyl, indenyl or alternatively 5-membered aromatic heterocycles such as furyl.

These radicals may also be substituted (one or more times) with groups containing hetero atoms, such as halogens, alkyloxy or nitro.

Thus, the use, by way of a carboxylic acid $R_2$—COOH or benzoic acid, according to the present invention, permits excellent protection of the OH group under excellent conditions of yield.

In addition, the presence of this group at the 5'-position promotes ring-opening by an alkali metal azide during the second stage of the process. It also makes it possible, in the case where it is desired to isolate the compound of formula (III), to obtain an insoluble product or at least a product which can be readily precipitated from the reaction solvent, by using, for example, a dissolving intermediary such as ether or an ester, or under reaction conditions favoring precipitation such as a small solvent volume and/or the use of a low temperature during the separation.

The temperature and pressure conditions of the reaction are not, strictly speaking, characteristic. In effect, the reaction may be performed at room temperature and at atmospheric pressure.

The reaction time naturally depends on the precise parameters employed but, more often than not, the reaction is complete after a few hours, although there is no disadvantage in leaving it for a longer period.

At the end of this first reaction stage, the compound of formula (III) is obtained, which compound can be either separated from the reaction mixture, as stated above, before undergoing the second stage, or alternatively, on the contrary, the reaction mixture can be treated directly, as will be described below.

The solvent for the reaction must be a solvent compatible with the reaction conditions. It will, more often than not, be an anhydrous polar aprotic solvent; as mentioned above, the presence of water can, in effect, seriously impair the yield of the process.

Among these solvents, DMF, HMPT and DMSO should be mentioned; on grounds of cost, DMF is the preferred solvent, in the light of the fact that it enables, in addition, the second stage of the process to be carried out without the need to separate the product formed in the first.

The different reactants are preferably used in molar excess relative to the compound of formula (II).

During the second preparation stage, the ring-opening reaction is performed in the presence of an excess of azide or cyanide. It is possible, in some cases, to decrease the excess of reactant by carrying out the reaction in the presence of a Lewis acid or another lithium salt. This reaction will preferably be carried out in the presence of only a slight excess of azide per mole of compound of formula (III), that is to say 1.5 equivalents.

The solvent used must permit solubilization both of the compound (III) and of the azide or cyanide used. It will generally be an anhydrous polar aprotic solvent, as mentioned above.

Thus, the reaction may be performed in DMF in the heated state in order to promote solubilization, for example at temperatures of the order of 100° C. up to the refluxing temperature which must remain compatible with the stability of the products involved; the reaction will then be complete in a few hours, that is to say approximately between 7 and 10 hours.

Alkali metal azides or alkali metal cyanides can be used in this reaction stage.

The separation of the compound of formula (I) obtained may be performed according to two methods.

The first consists in isolating it from the reaction mixture after the latter has been treated with an alkali metal hydrogen carbonate, for example by extraction with a halogenated solvent such as chloroform.

The organic phase is then washed with water, dried and evaporated in order to obtain a homogeneous product. This compound is then saponified and thereafter extracted.

It is naturally possible to saponify the product directly using the reaction medium of stage 2, and then, after separation of the different organic products and the different salts present, to recover the compound of formula (I), especially AZT, virtually quantitatively.

The examples below will enable other advantages and features of the present invention to be demonstrated.

EXAMPLE 1

The following mixture is added dropwise at room temperature (cooling should be applied for a larger amount) to 10 mmol of thymidine and 15 mmol of (Ph)$_3$P, in 25 ml of anhydrous DMF:

15 mmol of PhCOOH and 15 mmol of DEAD in 25 ml of anhydrous DMF. TLC (eluent A: AcOEt/MeOH, 20:1) shows that the reaction is complete in approximately 30 minutes. The 5'-position is then benzoylated.

The mixture is then treated successively with 15 mmol of (Ph)$_3$P and 15 mmol of DEAD (added slowly). The little further change in the reaction after 3 hours, but there is no disadvantage in leaving it for a longer period. TLC (eluent B: CHCl$_3$/EtOH, 4:1) shows the presence of (III), more polar than thymidine, and reaction byproducts (of very low polarity).

The isolation of the compound (III) is carried out very readily by pouring the reaction mixture (the possible presence of a precipitate does not interfere) into 250 ml of ether with stirring. The white precipitate is drained and washed with ether. 2.803 g of (III) (85.5%) are obtained.

(M.p. 242° C.; 1 spot in TLC (eluent B); IR and $^1$H NMR in agreement with the structure).

Treatment of the mother liquors (extraction or crystallization) enables more of compound (III) (10–13%) to be obtained. The product thus prepared is of satisfactory purity for performing the second stage.

EXAMPLE 2

2.46 g of (III) are treated with 1.5 g of LiN$_3$ (4 equivalents) in 20 ml of DMF under reflux. When the reaction is complete, the resulting mixture is poured into saturated sodium hydrogen carbonate solution (70 ml) and the white solid is extracted with chloroform (3×20 ml). After washing with water, drying and evaporation of the solvent, 2.7 g (96%) of product which is homogeneous in TLC are obtained.

This compound is saponified directly using 1.15 equivalents of MeONa in 50 ml of MeOH. When the reaction is complete, the mixture is poured into 30 ml of water and the methanol is evaporated off. The aqueous solution is extracted with ether (2×20 ml) to remove the methyl benzoate. Approximately 5 g of H$^+$ resin (Amberlite IRN-77) are added and the mixture is stirred at room temperature. When the pH is neutral, the solution is filtered and the solvent evaporated off. AZT is obtained quantitatively (1.940 g; approximately 100%). The compound obtained is homogeneous in TLC and its $^1$H NMR spectrum is in agreement with its structure.

EXAMPLE 3

The following mixture is added dropwise at room temperature to 2 mmol of thymidine and 3 mmol of $(Ph)_3P$ in 5 ml of anhydrous DMF:

3 mmol of an aromatic carboxylic acid $R_2COOH + 3$ mmol of DEAD in 5 ml of anhydrous DMF.

In the case where the acid $R_2COOH$ is insoluble in DMF, it is introduced into the medium at the same time as the thymidine.

TLC (eluent A: AcOEt/MeOH, 20:1) shows that the reaction is complete in 30 minutes.

The mixture is then treated successively with 3 mmol of $(Ph)_3P$ and 3 mmol of DEAD (added dropwise). The mixture is left stirring for 2 hours at room temperature. In the case where a precipitate is observed, the solid is drained, washed with ether and dried. Otherwise the procedure is as in Example 1.

The results are presented in the table below:

| $R_2$ | Quantity (yield) | M.p. (°C.) |
| --- | --- | --- |
| 2-furyl | 483 mg (76%) | 260 |
| 2-bromophenyl | 526 mg (64.5%) | 238 |
| 4-bromophenyl | 486 mg* (59.5%) | 300 |
| 4-nitrophenyl | 494 mg* (66%) | 300 |
| 3,5-dinitrophenyl | 758 mg (90.5%) | 258 |
| 4-methoxyphenyl | 546 mg* (82%) | 260 |
| 3,4-dimethoxyphenyl | 660 mg (84.5%) | 240 |
| 2,6-dichlorophenyl | 602 mg (76%) | 222 |

*First fraction obtained using the procedure described in Example 4.

EXAMPLE 4

The following mixture is added dropwise at room temperature to 5 mmol of thymidine and 7.5 mmol of $(Ph)_3P$ in 12.5 ml of DMF:

7.5 mmol of PhCOOH and 7.5 mmol of DIAD (diisopropyl azodicarboxylate) in 12.5 ml of DMF. TLC (eluent A:AcOEt/MeOH, 20:1) shows that benzoylation of the 5'-position is complete in 30 minutes.

The mixture is then treated succesively with 7.5 mmol of $(Ph)_3P$ and 7.5 mmol of DIAD (added dropwise). The mixture is left stirring at room temperature. There is little further change in the reaction after 2 hours, but there is no disadvantage in leaving it for a longer period. TLC (eluent B:CHCl$_3$/EtOH, 4:1) shows the presence of (III) and of reaction byproducts (of very low polarity).

The isolation of the compound (III) is carried out by pouring the reaction mixture into 125 ml of ether with stirring. The white precipitate is drained and washed with 25 ml of ether.

The compound (III) is obtained in an 83% yield.

Similarly, the isolation of the compound (III) may be carried out by pouring the reaction mixture into 125 ml of butyl acetate. The compound (III) will then be obtained in a 73% yield.

EXAMPLE 5

7.5 mmol of DIAD are added dropwise to a solution of 5 mmol of thymidine, 7.5 mmol of $(Ph)_3P$ and 7.5 mmol of PhCOOH in 12.5 ml of DMF.

After approximately 30 minutes, TLC (eluent A: AcOEt/MeOH, 20:1) shows that the thymidine has disappeared.

The mixture is then treated successively with 7.5 mmol of $(Ph)_3P$ and 7.5 mmol of DIAD (added dropwise). The mixture is left stirring for 1 hour at room temperature and the precipitate formed is filtered off. The solid is washed with 25 ml of ether and dried.

0.955 g of (III) (58.2%) is obtained. A second fraction of (III) is obtained by pouring the mother liquors into 125 ml of ether with stirring. Filtration yields 0.24 g of (III) (14.6%).

The total quantity of (III) obtained is 1.195 g (73%).

EXAMPLE 6

2.434 g of (III:$R_2$=Ph) are dissolved in 15 ml of DMF at 140° C. 544 mg of LiN$_3$ (1.5 equivalents) are then added. After 4 h of heating at this temperature, the reaction is complete. The resulting mixture is diluted with 40 ml of chloroform and the solution is extracted with 75 ml of saturated aqueous sodium hydrogen carbonate solution. The aqueous solution is extracted with chloroform (3×35 ml). After washing with water, drying and evaporation of the solvent, 5'-benzoylated AZT is obtained quantitatively. The compound is homogeneous in TLC, and contains traces of DMF which do not interfere in the next stage.

EXAMPLE 7

2 g of (III:$R_2$=Ph) are treated with 2.7 g of LiN$_3$ (9 equivalents) in 16 ml of anhydrous DMF at 110° C. When the reaction is complete, the resulting mixture is treated as in Example 3. 2.509 g of product which is homogeneous in TLC are thereby obtained, the $^1$H NMR spectrum (90 MHz) of which product indicates the presence of 12% of DMF. The conversion is hence quantitative.

EXAMPLE 8

2.1 g of 5'-benzoyl-3'-azidothymidine (containing 8.5% of DMF) are dissolved in the heated state in 20 ml of methanol. 1.15 equivalents of molar MeONa in methanol (6.6 ml) are then added. The solution is left at room temperature. When the reaction is complete, the mixture is poured into 30 ml of water and the methanol is evaporated off. The aqueous solution is extracted with ether (2×20 ml) to remove the methyl benzoate. The solution is then neutralized using approximately 2 g of Amberlite IRN-77 (H+) resin. After filtration and evaporation of the solvent, 1.424 g (94%) of AZT are obtained.

EXAMPLE 9

2.1 g of 5'-benzoyl-3'-azidothymidine (containing 8.5% of DMF) are treated with 6.6 ml of molar MeONa in methanol as in Example 8. When the reaction is complete, the methanol is evaporated off and 50 ml of water are added. The mixture is subjected to steam distillation to remove the methyl benzoate. The aqueous phase is then neutralized and treated as in Example 5. 1.422 g (94%) of AZT which is homogeneous in TLC are obtained.

EXAMPLE 10

2.434 g of (III:$R_2$=Ph) are treated with 1.5 equivalents of LiN$_3$ as in Example 6. The resulting product, which contains traces of DMF, is treated with 20 ml of water and 7.5 ml of 3M sodium hydroxide in a methanol/water (1:1) mixture. The mixture is stirred at room temperature. When the reaction is complete, the solution is neutralized with the calculated amount of concentrated HCl. The solution is saturated with NaCl and extracted with ethyl acetate (3×30 ml). The organic phase is dried and the solvent evaporated off after filtration. 2.164 g of crude product, which contains traces of DMF and AcOEt, a little benzoic acid ($^1$H NMR) and at least 1.78 g of AZT, are obtained.

EXAMPLE 11

1.19 g of (III:$R_2$=Ph) are dissolved in 5 ml of DMF at 140° C. 470 mg of NaN$_3$ (2 equivalents) are then added. After 7 hours' heating at this temperature, the reaction is complete. The mixture is treated as in Example 6. 1.439 g of a product which is homogeneous in TLC, containing 7% of DMF, are obtained. The conversion is quantitative.

We claim:

1. Process for preparing a compound of formula (I)

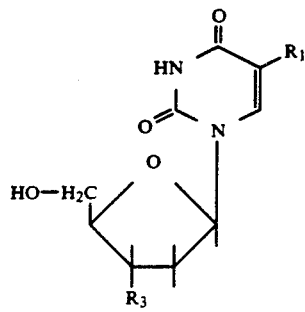

in which $R_1$ is H, a lower alkyl, lower alkoxy, or lower hydroxyalkyl, all three containing from 1 to 5 carbon atoms, or halogen radical, and $R_3$ is $N_3$ or a CN radical, characterized in that a compound of formula (II):

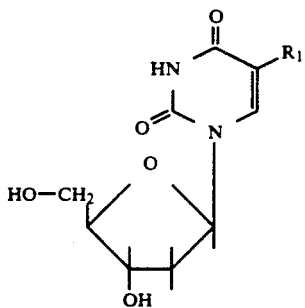

is reacted with a phosphine derivative and an azodi-carboxylic acid diester and a carboxylic acid $R_2$—COOH where $R_2$ is phenyl or phenyl substituted with one or more halogen, alkyloxy or nitro groups, in an anhydrous polar aprotic solvent, to form the compound of formula (III):

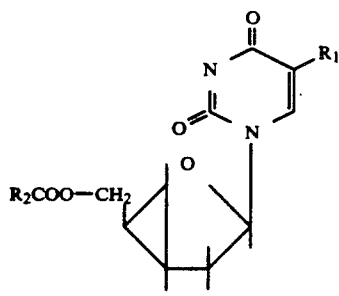

which, after separation if required, is opened in the presence of an azide or a cyanide in a solvent compatible with the reaction conditions, and the compound of formula (I) is then isolated from the reaction medium after deprotection of the 5'-position.

2. Process according to claim 1, characterized in that the phosphine used is triphenylphosphine.

3. Process according to claim 1, characterized in that the azodicarboxylic acid diester is an alkyl.

4. Process according to claim 3, characterized in that the diester is a lower alkyl ester.

5. Process according to claim 1, characterized in that the reaction solvent is an anhydrous polar aprotic solvent.

6. Process according to claim 5, characterized in that the solvent is chosen from DMF, HMPT and DMSO.

7. Process according to claim 1, characterized in that the product (III) is separated from the reaction mixture by precipitation.

8. Process according to claim 7, characterized in that the precipitation of the compound (III) can be obtained by adding an ether or an ester to the reaction medium.

9. Process according to claim 1, characterized in that the reactants are used in molar excess relative to the compound (II).

10. Process according to claim 1, characterized in that the compound of formula (III) is not separated from the reaction medium.

11. Process according to claim 1, characterized in that the compound of formula (III) is treated with an excess of azide or of cyanide in a polar aprotic solvent.

12. Process according to claim 1, characterized in that the compound of formula (III) is treated with 1.5 equivalents of alkali metal azide in DMF.

13. Process according to claim 1, characterized in that the product is recovered after saponification and neutralization.

14. A compound of formula III:

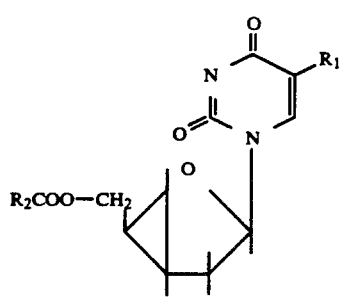

in which $R_1$ is lower alkoxy or lower hydroxyalkyl, both containing from 1 to 5 carbon atoms, or halogen radical, $R_2$ is phenyl or phenyl substituted with one or more halogen, alkyloxy or nitro groups.

15. A process for the preparation of a compound of formula III:

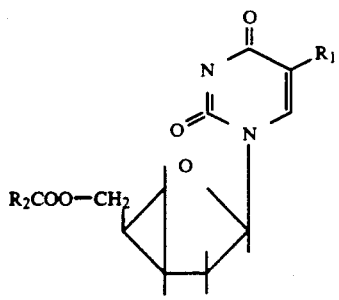

in which $R_1$ is selected from the group consisting of H, an alkyl radical, an alkoxy radical, hydroxyalkyl and halogen radical, $R_2$ is phenyl or phenyl substituted with one or more halogen, alkyloxy or nitro groups, wherein a compound of formula II:

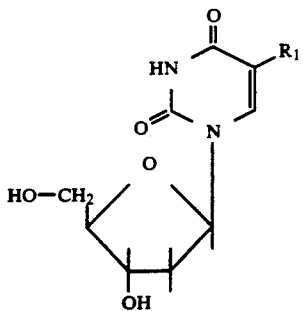

in which $R_1$ is selected from the group consisting of H, an alkyl radical, an alkoxy radical, hydroxyalkyl and halogen radical, is reacted with a phosphine derivative and an azo-dicarboxylic acid diester and a carboxylic acid $R_2$—COOH in which $R_2$ is phenyl or phenyl substituted with one or more halogen, alkyloxy or nitro groups, said carboxylic acid being in a solvent compatible with the reaction conditions, with the proviso of excluding the compound of formula III and formula II in which $R_1$ is a methyl group and $R_2$ is a phenyl or nitrophenyl group.

* * * * *